(12) United States Patent
Bander et al.

(10) Patent No.: US 6,653,129 B1
(45) Date of Patent: Nov. 25, 2003

(54) METHOD FOR ISOLATION OF CELLS FROM A SOLUTION

(75) Inventors: Neil H. Bander, Chappaqua, NY (US); Leonard Michael Glode, Golden, CO (US); Chang In Suh, Seoul (KR)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 09/655,708

(22) Filed: Sep. 6, 2000

Related U.S. Application Data
(60) Provisional application No. 60/153,506, filed on Sep. 13, 1999.

(51) Int. Cl.[7] .............................. C12N 5/00; C12N 5/06; C12N 5/22
(52) U.S. Cl. ..................... 435/325; 435/326; 435/344.1
(58) Field of Search .......................... 435/4, 173.9, 325, 435/326, 344.1; 530/388.1

(56) References Cited

U.S. PATENT DOCUMENTS 5,538,866 A * 7/1996 Israeli et al. ................ 435/69.3

FOREIGN PATENT DOCUMENTS

WO    WO 98/03873   *   1/1998  ............... 435/7.23

OTHER PUBLICATIONS

Martin et al. Enrichment of epithelial tumor cells from peripheral blood and bone marrow of carcinoma patients by high gradient magnetic cell sorting (MACS). Proc. Am. Ass. for Cancer Res. Annual Mtg. Vol 38(0):p492, Apr. 1997.*

Griwatz et al. An immunological enrichment method for epithelial cells from peripheral blood. J. Imm. Methods. vol. 183:251–265, 1995.*

* cited by examiner

*Primary Examiner*—Remy Yucel
*Assistant Examiner*—William Sandals
(74) *Attorney, Agent, or Firm*—Fish & Richardson P.C.

(57) ABSTRACT

The present invention relates to methods for the isolation of prostatic cancer tumor cells from a biological fluid, using a magnetic activated cell sorter (MACS).

16 Claims, 1 Drawing Sheet

METHOD FOR ISOLATION OF CELLS FROM A SOLUTION

RELATED APPLICATION DATA

This application claims priority from application Ser. No. 60/153,506 filed Sep. 13, 1999.

FIELD OF THE INVENTION

The present invention is directed to a method for the isolation and detection of normal, benign hyperplastic, and cancerous prostate epithelial cells from semen, using a magnetic activated cell sorter (MACS).

BACKGROUND OF THE INVENTION

In spite of improved treatments for certain forms of cancer, it is still a leading cause of death in the United States. Since the chance for complete remission of cancer is, in most cases, greatly enhanced by early diagnosis, it is very desirable that physicians be able to detect cancers before a substantial tumor develops. However, the development of methods that permit rapid and accurate detection of many forms of cancer continues to challenge the medical community. One such illustrative form of cancer is prostate cancer.

Prostate cancer is the most common cancer in men with an estimated 317,000 cases in 1996 in the United States. It is the second leading cause of death among men who die from neoplasia with an estimated 40,000 deaths per year. Prompt detection and treatment is needed to limit mortality caused by prostate cancer.

Screening tests (i.e., digital rectal examination and prostatic specific antigen levels) are widely used for early detection of potentially curable prostatic cancer, but an accurate cytologic or histologic assessment is necessary to confirm the proper and accurate diagnosis. A prostatic needle biopsy is specific, but invasive and has a significant false negative rate (Stroumbakis, N. et al., *Urology*, 49 (Suppl. 3A):113–118 (1997)). Furthermore, this procedure is associated with a significant level of morbidity, such as infection and bleeding.

Detection of Prostate Cancer

When it metastasizes, prostatic cancer has a distinct predilection for bone and lymph nodes (Saitoh et al., *Cancer*, 54:3078–3084 (1984)). At the time of clinical diagnosis, as many as 25% of patients have bone metastasis demonstrable by radionuclide scans (Murphy, G. P., et al., *J. Urol.*, 127:928–939 (1982)). Accurate clinical evaluation of nodal involvement has proven to be difficult. Imaging techniques such as computed tomography ("CT") or magnetic resonance ("MR") imaging are unable to distinguish metastatic prostate cancer involvement of lymph nodes by criterion other than size (i.e., >1 cm). Therefore, by definition, these imaging modalities are inherently insensitive in the detection of small volume (<1 cm) disease as well as non-specific in the detection of larger volume adenopathy. A recent study assessed the accuracy of MR in patients with clinically localized prostate cancer (Rifkin et al., *N. Engl. J. Med.*, 323:621–626 (1990)). In this study, 194 patients underwent a MRI examination and 185 of these patients had a lymph node dissection. Twenty-three (13%) of the patients had pathologically involved lymph nodes. MRI was suspicious in only 1 of these 23 cases, resulting in a sensitivity of 4%. Similar results have also been noted with CT scans (Gasser et al., *N. Engl. J. Med.* (*Correspondence*), 324(7): 49–495 (1991)).

The elevation of serum acid phosphatase activity in patients having metastasized prostate carcinoma was first reported by Gutman et al., *J. Clin. Invest.*, 17:473 (1938). In cancer of the prostate, prostatic acid phosphatase is released from the cancer tissue into the blood stream with the result that the total serum acid phosphatase level can be greatly increased above normal values. Numerous studies of this enzyme and its relation to prostatic cancer have been made since that time, e.g. Yan, *Amer. J. Med.*, 56:604 (1974). However, the measurement of serum acid phosphatase is elevated in about 65–90 percent of patients having carcinoma of the prostate with bone metastasis; in about 30 percent of patients without roentgenological evidence of bone metastasis; and in about only 5–10 percent of patients lacking clinically demonstrable metastasis.

Prior art attempts to develop a specific test for prostatic acid phosphatase have met with only limited success, because techniques which rely on enzyme activity on a so-called "specific" substrate cannot take into account other biochemical and immunochemical differences among the many acid phosphatases which are unrelated to enzyme activity of prostate origin. In the case of isoenzymes, i.e., genetically defined enzymes having the same characteristic enzyme activity and a similar molecular structure but differing in amino acid sequences and/or content and, therefore, immunochemically distinguishable, it would appear inherently impossible to distinguish different isoenzyme forms merely by the choice of a particular substrate. It is, therefore, not surprising that none of these prior art methods is highly specific for the direct determination of prostatic acid phosphatase activity (*Cancer* 5:236 (1952); *J. Lab. Clin. Med.*, 82:486 (1973); *Clin. Chem. Acta*, 44:21 (1973); and *J. Physiol. Chem.*, 356:1775 (1975)).

In addition to the aforementioned problems of non-specificity, which appear to be inherent in many of the prior art reagents employed for the detection of prostate cancer phosphatase, there have been reports of elevated serum acid phosphatase associated with other diseases, which further complicates the problem of obtaining an accurate clinical diagnosis of prostatic cancer. For example, Tuchman et al. noted that serum acid phosphatase levels appear to be elevated in patients with Gaucher's disease (Tuchman et al., *Am. J. Med.*, 27:959 (1959)).

Due to the inherent difficulties in developing a "specific" substrate for prostate acid phosphatase, several researches have developed immunochemical methods for the detection of prostate acid phosphatase. However, the previously reported immunochemical methods have drawbacks of their own which have precluded their widespread acceptance. For example, Shulman et al. described an immunodiffusion test for the detection of human prostate acid phosphatase (Shulman et al., *Immunology*, 93:474 (1964)). Using antisera prepared from a prostatic fluid antigen obtained by rectal massage from patients with prostatic disease, no cross-reactivity precipitin line was observed in the double diffusion technique against extracts of normal kidney, testicle, liver, and lung. However, this method has the disadvantages of limited sensitivity, even with the large amounts of antigen employed, and of employing antisera which may cross-react with other, antigenically unrelated serum protein components present in prostatic fluid.

WO 79/00475 to Chu et al. describes a method for the detection of prostatic acid phosphatase isoenzyme patterns associated with prostatic cancer which obviates many of the above drawbacks. However, practical problems are posed by this method, such as the need for a source of cancerous prostate tissue from which the diagnostically relevant prostatic acid phosphatase isoenzyme patterns associated with prostatic cancer are extracted for the preparation of antibodies thereto.

In recent years, considerable effort has been spent to identify enzyme or antigen markers for various types of malignancies with the view towards developing specific diagnostic reagents. Previous investigators have demonstrated the occurrence of human prostate tissue-specific antigens. The ideal tumor marker would exhibit, among other characteristics, tissue or cell-type specificity.

Use of Monoclonal Antibodies in Prostate Cancer Detection and Treatment

Theoretically, radiolabeled monoclonal antibodies ("mAbs") offer the potential to enhance both the sensitivity and specificity of detecting prostatic cancer within lymph nodes and elsewhere. While many mAbs have previously been prepared against prostate related antigens, none of these mAbs were specifically generated with an imaging objective in mind. Nevertheless, the clinical need has led to evaluation of some of these mAbs as possible imaging agents (Vihko et al., *Biotechnology in Diagnostics*, 131–134 (1985); Babian et al., *J. Urol.*, 137:439–443 (1987); Leroy et al., *Cancer*, 64:1–5 (1989); Meyers et al., *The Prostate*, 14:209–220 (1989)).

In some cases, the monoclonal antibodies developed for detection and/or treatment of prostate cancer recognize antigens specific to malignant prostatic tissues. Such antibodies are thus used to distinguish malignant prostatic tissue (for treatment or detection) from benign prostatic tissue. See U.S. Pat. No. 4,970,299 to Bazinet et al. and U.S. Pat. No. 4,902,615 to Freeman et al.

Other monoclonal antibodies react with surface antigens on all prostate epithelial cells whether cancerous or benign. See U.S. Pat. Nos. 4,446,122 and Re 33,405 to Chu et al., U.S. Pat. No. 4,863,851 to McEwan et al., and U.S. Pat. No. 5,055,404 to Ueda et al. However, the antigens detected by these monoclonal antibodies are present in the blood and, therefore, compete with antigens at tumor sites for the monoclonal antibodies. This causes background noise which makes the use of such antibodies inadequate for in vivo imaging. Furthermore, such antibodies, if bound to a cytotoxic agent, could be harmful to other organs if used in therapy.

Horoszewicz et al., *Anticancer Research*, 7:927–936 (1987) (hereinafter "Horoszewicz") and U.S. Pat. No. 5,162,504 to Horoszewicz describe an antibody, designated 7E11, which recognizes prostate specific membrane antigen ("PSMA"). Israeli et al., *Cancer Research*, 53:227–230 (1993) (hereinafter "Israeli") describes the cloning and sequencing of PSMA and reports that PSMA is prostate-specific and shows increased expression levels in metastatic sites and in hormone-refractory states. Other studies have indicated that PSMA is more strongly expressed in prostate cancer cells relative to cells from the normal prostate or from a prostate with benign hyperplasia. Furthermore, PSMA is not found in serum (Troyer et al., *Int. J. Cancer*, 62:552–558 (1995)).

These characteristics make PSMA an attractive target for antibody-mediated targeting for imaging and therapy of prostate cancer. Imaging studies using indium-labeled 7E11 have indicated that the antibody localizes quite well to both the prostate and to sites of metastasis. In addition, 7E11 appears to have clearly improved sensitivity for detecting lesions compared to other currently available imaging techniques, such as CT and MR imaging or bone scan (Bander, N. H., *Sem. in Oncology*, 21:607–612 (1994)).

However, the use of 7E11 and other known antibodies to PSMA to mediate imaging and therapy has several disadvantages. First, PSMA is an integral membrane protein known to have a short intracellular tail and a long extracellular domain. Biochemical characterization and mapping studies (Troyer et al., *Urol. Oncol.*, 1:29–37 (1995)) have shown that the epitope of the antigenic site to which the 7E11 antibody binds is present on the intracellular portion of the PSMA molecule. Because antibody molecules do not, under normal circumstances, cross the cell membrane unless they bind to the extracellular portion of a molecule and become translocated intracellularly, the 7E11 antibody does not have access to its antigenic target site in an otherwise healthy, viable cell.

Consequently, imaging using 7E11 is limited to the detection of dead cells within tumor deposits. What is needed is a method to separate living, viable prostatic cells from tissues or fluids to enhance the detection of malignant prostatic cells.

Although the inadequacies and problems in the diagnosis and treatment of one particular type of cancer are the focus of the preceding discussion, prostate cancer is merely a representative model. The diagnosis and treatment of numerous other cancers have similar problems. Therefore, a method to enhance the separation of malignant cells from biological fluids that is applicable to a wide variety of cancers would be even more desirable.

Separation of Prostatic Epithelial Cells From Biological Fluids

An antibody against the prostate-specific antigen ("PSA") has been used to select prostate cells. However, due to the absence of PSA from cell surface membranes, and due to the large concentration of PSA protein in semen, the antibody to PSA is known to stain nonepithelial cells in addition to the cytokeratin-positive populations (Barren, III, R. J. et al., *Prostate*, 36:181–188 (1998)). Moreover, whereas PSA protein is known to be more highly expressed by differentiated prostatic epithelial cells, PSMA protein is highly expressed in undifferentiated prostatic epithelial cells and tumors (Bostwick, D. G. et al., *Cancer*, 82:2256–2261 (1998)).

Copending U.S. patent applications Ser. Nos. 08/838,682 now U.S. Pat. No. 6,107,090, and 08/895,914 now U.S. Pat. No. 6,136,311, which are hereby incorporated in their entirety, describe procedures for detecting and ablating or killing normal, benign hyperplastic, and cancerous prostate epithelial cells. The method employs a biological agent, such as an antibody or a binding portion of an antibody, to bind an extracellular domain of the PSMA protein on such cells. The biological agent is contacted with the cells under conditions that allow both binding of the biological agent to the PMSA protein on the cells for detecting and ablating or killing of the cells. The biological agent may be used alone or in combination with a substance effective to kill the cells. The biological agent may also be used to detect normal, benign hyperplastic, or cancerous prostate epithelial cells, or portions thereof, in a biological sample.

Previously, a modified ficoll-hypaque separation procedure and sorting by flow cytometry was used to separate prostatic epithelial cells from semen. By ficoll-hypaque gradient separation, separation of intentionally added cancer cells from fresh semen was achieved but the recovery rate was highly variable. By flow cytometry this cell separation based on size and granularity identified by light scatter characteristics was accomplished. The fact that the target cell population could be isolated without requiring the use of fluorescent dyes (which may have interfered with subsequent assays) was significant. However, the recovery of prostate epithelial cells was not consistent (unpublished observation).

The present invention therefore, provides an improved method to isolate normal, benign hyperplastic, or cancerous prostate epithelial cells from semen.

SUMMARY OF THE INVENTION

The present invention provides a method for the isolation of epithelial cells from a solution, comprising providing a biologic agent capable of binding to an extracellular domain of prostate specific membrane antigen (PSMA), contacting the biologic agent with a magnetizable medium under conditions permitting binding of the biologic agent to the magnetizable medium, contacting a solution containing the epithelial cells with the magnetizable medium under conditions permitting binding of the biologic agent to the epithelial cells to form a complex including the magnetizable medium, the biologic agent, and the epithelial cells, contacting the complex with a magnetized matrix under conditions permitting removal of the complex from the solution, and eluting the epithelial cells from the magnetized matrix. The biologic agent may be a polyclonal antibody, a monoclonal antibody, or a portion of a monoclonal antibody, such as an F(ab) fragment, an F(ab')$_2$ fragment, or an F$_v$ fragment. The biologic agent may also be a probe or a ligand capable of binding to PMSA. The biologic agent is preferably a monoclonal antibody or a portion thereof that binds specifically to the extracellular domain of PSMA, such as mAb E99, mAb J415, mAb J533, or mAb J591. The biologic agent is more preferably a monoclonal antibody or a portion thereof of mAb J591. The monoclonal antibodies, polyclonal antibodies, and portions thereof may be produced by methods that are well known to those in the art.

The present invention also provides a method for detecting the presence of cancerous vascular endothelial cells, comprising providing a biologic agent capable of binding to an extracellular domain of prostate specific membrane antigen (PSMA), contacting the biologic agent with a magnetizable medium under conditions permitting binding of the biologic agent to the magnetizable medium, contacting a solution containing the cancerous vascular endothelial cells with the magnetizable medium bound to the biologic agent under conditions permitting binding of the biologic agent to the cancerous vascular endothelial cells to form a complex containing the magnetizable medium, the biologic agent, and the cancerous vascular endothelial cells, contacting the complex with a magnetized matrix under conditions permitting isolation of the complex from the solution, eluting the epithelial cells from the magnetized matrix, and detecting the presence of the cancerous vascular endothelial cells.

The epithelial cells in the solution may be normal epithelial cells, benign hyperplastic epithelial cells, cancerous epithelial cells, normal prostate epithelial cells, benign hyperplastic prostate epithelial cells, or cancerous prostate epithelial cells. The method is particularly applicable to the isolation of cancerous prostate epithelial cells, such as prostatic adenocarcinoma cells.

The epithelial or vascular endothelial cells may be contained in any appropriate fluid, including a biological fluid or a tissue culture fluid. The biological fluid may be blood, urine, semen, seminal fluid, lymph, cerebrospinal fluid, mucus, tears, sweat, gastric fluid, saliva, synovial fluid, or a bone marrow suspension.

BRIEF DESCRIPTION OF THE DRAWINGS

FIG. 1A—Cells before separation. FIG. 1B—the positive fraction eluted after removal from magnetic field. FIG. 1C—the negative fraction which flowed through the column. Region R1 contains prostasomes and cell fragments; Region R2 contains PSMA positive prostate epithelial cells; and Region R3 contains mature spermatozoa.

DETAILED DESCRIPTION OF THE PREFERRED EMBODIMENTS

Figure 1A:
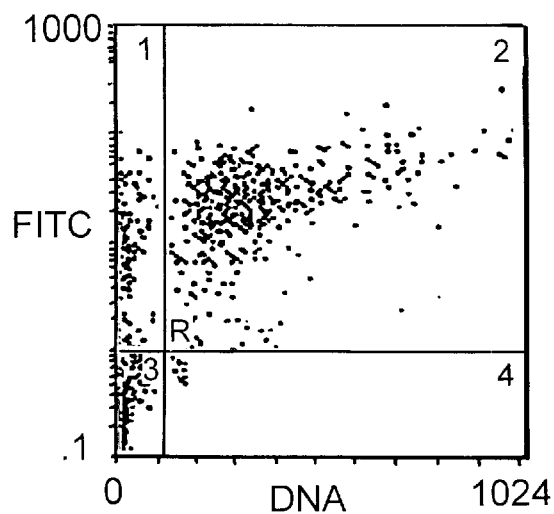
FIGS. 1A–1C show flow cytometric analysis of semen spiked with cultured prostate cancer cells (LNCaP) before and after treatment according to the method of the present invention. The cells were passed down a magnetic activated cell sorter (MACS) separating column.

In an attempt to find a more sensitive and noninvasive assay for the detection of prostatic cancer, we assayed exfoliated cells from patients' semen. Because the semen contains prostate epithelial cells (Barren III, R. J., et al., *Prostate*, 36:181–188 (1998)) and is easily obtainable, it could provide a source for additional prostate tumor cell studies. In addition, the isolation of malignant cells in semen could facilitate the diagnostic evaluation of patients in whom initial biopsies are negative in spite of a high index of suspicion. Finally, such cells might be repetitively sampled, during therapy, with various molecular techniques.

The inventors have discovered that magnetic activated cell sorting (MACS) provides an improved method of cell separation over techniques employed in the prior art. MACS is versatile and innocuous to the cells (Miltenyi, S. et al., *Cytometry*, 11:231–238(1990)). MACS has found many useful applications in immunological research, especially in separating lymphocyte subsets based on their expression of cell surface antigens. The technique involves coupling the cell surface with biodegradable microbeads the size of cellular macromolecules (50–150 nm diameter). The cells are then passed through a magnetizable matrix in a strong magnetic field. Labeled cells stick to the matrix and are separated from unlabeled cells, which flow through. The magnetic labeled tumor cells can be eluted when the column is demagnetized by removal from the magnetic field (Wong, L. S., et al., *Brit. J. Surg.*, 82:1333–1337 (1995)). A device for practicing the technique can be obtained from Miltenyi Biotec, Bergisch Gladbach, Germany.

Prostate specific membrane antigen (PSMA) is a novel prostate epithelial cell marker. PSMA is known to be overexpressed in poorly differentiated and metastatic prostate carcinoma and apparently upregulated following hormone-ablation therapy (Bostwick, 1998). An anti-PSMA antibody to identify prostate cancer cells in semen was used. As a model for semen from patients with prostatic cancer, semen from normal volunteers spiked with LNCaP cells was used.

EXPERIMENTAL RESULTS

Materials and Methods

1. Neoplastic Cell Lines and Semen Samples:

Well-characterized human prostate cancer cell lines, LNCaP and DU145 (ATCC, Rockville, Md.) were propagated in vitro in RPMI 1640 media supplemented with 10% fetal bovine serum (FBS) (Life Technologies, Inc. Gaithersburg, Md.) at 37° C. in 5% $CO_2$. Cells were haryested by exposure to 0.25% trypsin. Semen samples were donated from volunteers without objective evidence of prostatic cancer. All volunteers provided written informed consent for the protocol, which was approved by the institutional review board.

2. Monoclonal Antibody J591:

Monoclonal antibody (mAb) J591 supernatant was produced as a supernatant from cell culture as previously described (Liu, H. et al., *Cancer Res.*, 57:3629–3634 (1997)). This mAb is an IgG1 of mouse origin and known to define an epitope on the extracellular domain of PSMA (Liu, 1997).

3. Magnetic Activated Cell Sorting (MACS):

Semen samples were diluted to 9 ml with phosphate buffered saline (PBS) containing 0.5% bovine serum albumin (BSA) and 2 mM EDTA (Buffer A), aliquoted into three tubes and $10^3$ or $10^4$ LNCaP cells were added to two tubes. After centrifugation at 78 xg for 5 min, the supernatant (which contains most prostasomes and some spermatozoa) was removed, and the pellet (mostly spermatozoa and epithelial cells) was resuspended in 100 µl of Buffer A and then 100 µl of J591 supernatant was added. The mixture was incubated for 45 min at 4° C. After washing twice with Buffer A and pelleting, the cells were resuspended in 80 µl Buffer A to which 20 µl of rat anti-mouse IgGl magnetized microbeads (Miltenyi Biotec) were added. The mixture was incubated for 30 min at 4° C. Cells were then washed twice, resuspended in 500 µl of Buffer A and passed through the MACS RS+ separation column in a high strength magnetic field (Vario MACS, Miltenyi Biotec). Labeled cells attach to the magnetized matrix in the column, and unlabeled cells were washed out with 2.5 ml of Buffer A. The effluent was collected as the negative fraction. After the column had been removed from the magnetic field, the magnetically labeled cells were eluted with 1 ml of Buffer A. The quality of separation was assessed by flow cytometry and cytology.

4. Flow Cytometric Analysis:

The efficacy of sorting of epithelial cells was determined by flow cytometry (EPICS XL, Coulter, Hialeah, Fla.) using a fluorescein isothiocyanate (FITC)-conjugated goat anti-mouse Ig (Becton Dickinson, San Jose, Calif., U.S.A.) as a secondary antibody. To differentiate PSMA-positive cell debris and prostasomes from intact PSMA-positive cells, we fixed cells with 1% paraformnaldehyde and stained DNA with propidium iodide (25 µg/ml).

5. Staining of Cells for Cytology:

For the cytologic studies, the cell pellet was spun on a Shandon Cytospin® 3 centrifuge (Shandon Scientific Ltd., Runcorn, England) after placing the cells on coated slides using Saccomanno fixative (Fisher Scientific Co.). Immunocytochemical staining was performed for leukocyte common antigen and prostate specific antigen (PSA). Additionally, some slides were prepared with Papanicolaou stain.

6. Recovery Experiments:

Variable numbers ($10^4$, $10^5$, or $10^6$) of LNCaP cells were added to semen samples and processed as above. Cell numbers were counted by a hemacytometer. The recovery rate was determined as the absolute number of LNCaP cells in the enriched fraction in relation to the initially added quantity and expressed as percentage.

Results:

1. J591 Binding to Prostate Cancer Cells:

To confirm that J591 supernatant binds to prostate cancer cells, immuno-cytochemistry was performed on LNCaP and DU145 cells. J591 staining showed strong cytoplasmic and membranous staining of LNCAP cells, but not of DU145 cells, in agreement with results published previously (Israeli, R. S. et al., *Cancer Res.*, 54:1807–1811 (1994)).

2. Recovery Experiments:

Using the method of the present invention, a recovery rate of 11 to 42 percent of tumor cells added was obtained, as measured by counting in a hemacytometer. There was a tendency for increased recovery rate upon increasing the initially added cell count. The moderate recovery rate can be explained by loss of cells and damage to tumor cells during washing and labeling procedures. Considering only the column passage step, recovery rates varied from 25 to 87%. The presence of semen (cells in culture media only versus cells added in semen) or sperm (normal semen with sperm versus aspermnic semen) did not change the recovery rate significantly. This suggests that affinity between cells and antibody and microbeads would not be altered greatly by sperm or seminal plasma.

Figure 1B:
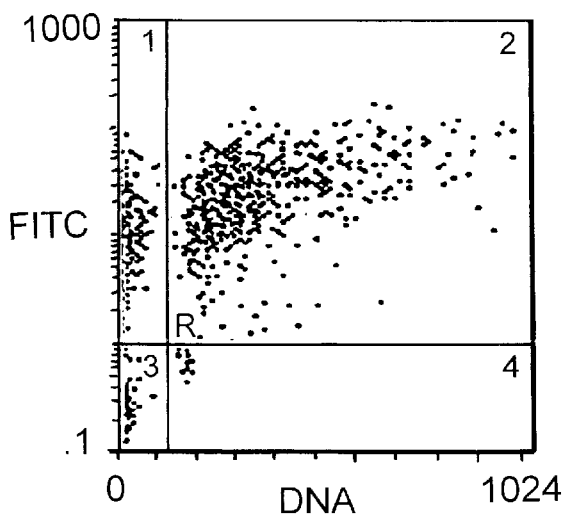
Figure 1C:
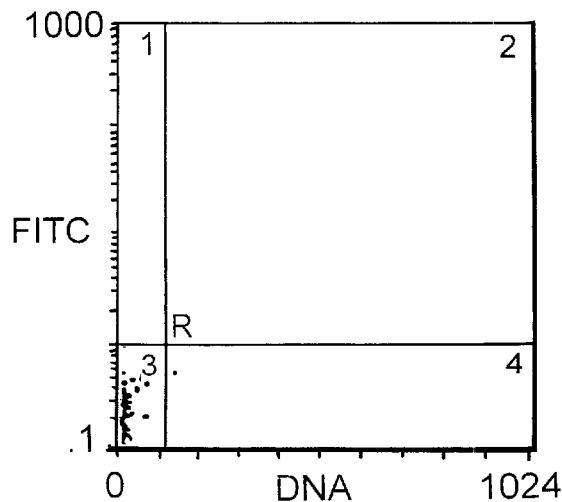

3. Flow Cytometry and Cytolopic Analysis of MACS Isolated Cells:

A total of $5\times10^4$ LNCaP cells were mixed with semen (LNCaP to sperm ratio was 1:34). The collected positive fractions and negative fractions were assessed by conventional cytology (the cells were stained with Papanicolaou stain) and flow cytometry (FIG. 1). Before MACS, there were many sperm admixed with LNCaP cells. After separation, mpst sperm had been removed from the semen. Prostasomes, presumably positive for PSMA, were also concentrated in this technique. For the flow cytometry analysis, the forward scatter (size) versus side scatter (granularity) graph was used to include all cellular elements. Events gated were then represented on a two-dimensional log graph. For fluorescence sorting, the propidium iodide staining for DNA was represented horizontally, and PSMA staining was represented vertically. As shown in FIG. 1B, the PSMA positive cell purity of positive fraction was about 40–50% by flow cytometry. By cytologic evaluation, the R1 region was found to be prostasomes and dead cell fragments. An increased percentage of events in R1 after column sorting can be explained by mechanical damage during the multistep procedure. As shown, by dual action of MACS and flow cytometric sorting, sorted cells from R2 were nearly pure LNCaP cells. The R4 region was hypothesized to be PSMA-negative intact cells, such as leukocytes, but due to low cell count in normal semen, we could not confirm these components. As shown in FIG. 1C, there were very few tumor cells in the negative fraction.

Discussion:

PSMA was initially defined by mAb 7E11 (Horoszewicz). MAb 7E11 has been shown to bind an intracellular epitope of PSMA that is not available for binding in viable cells; it binds to PSMA when cells undergo apoptosis or necrosis and the integrity of the membrane is disrupted (Troyer, J. K., et al., *Prostate*, 30:232–242 (1997)). The antibody that was employed in this study, J591, binds the external domain of PSMA and therefore can be used to target viable cells (Liu, H. et al., *Cancer Res.*, 57:3629–3634 (1997)). Using PSMA, normal prostatic epithelial cells as well as prostate cancer cells can be identified and collected. The proportion of shed normal epithelial cells is thought to be negligible, based on previous cytologic studies (Barren, 1998; Gardiner, R. A. et al,. *Br. J. Urol.*, 78:414–418 (1996)).

In contrast to the observation that benign and neoplastic prostatic epithelial cells were immunoreactive for PSMA in all cases stained (Bostwick et al., 1998), Israeli et al. noted heterogeneous and at times absent PSMA expression in benign prostatic hyperplasia (Israeli, 1994). Even more, DU145 and PC3 prostatic cancer cell lines do not have PSMA expression (Israeli, 1994). Therefore, we can not exclude the possibility of missing PSMA-negative malignant cells. In spite of this possibility, the method used in this study will work for the substantial majority of patients' semen to collect viable prostatic epithelial cells that can be used for further characterization. It remains to be determined whether markers for malignancy such aneuploidy (van Dekken, H. et al., *Histochem Cell Bio.*, 108:419–430

(1997)), hypermethylation of the glutathione S-transferase π1 promoter region (Lee, W-H., et al., *Proc. Natl. Acad. Sci. USA*, 91:11733–11737 (1994)), or expression of telomerase (Sommerfeld, H., et al., *Cancer Res.*, 56:218–222 (1997)) might suffice to identify prostatic cancer cells shed into semen.

The method of the present invention can be used to screen patient for diseases associated with the presence of normal, benign hyperplastic, and cancerous epithelial cells or portions thereof. Alternatively, it can be used to identify the recurrence of such diseases. The biological agent of the present invention can also be contacted with a biological sample, such as serum, blood or urine, to ascertain whether any vascular endothelial cells expressing an extracellular domain of prostate specific membrane antigen are present therein. Since vascular endothelial cells expressing an extracellular domain of prostate specific membrane antigen are found in the vasculature of cancerous tissues but not in the vasculature of normal tissues, detection of the label in a serum or urine sample indicates the presence of cancerous tissue in the patient. The methods of the present invention can be used to detect cancerous prostate epithelial cells as well as cancerous tissues containing cancerous cells other than cancerous prostate epithelial cells. Examples of cancerous tissues containing cancerous cells other than cancerous prostate epithelial cells which can be detected with the methods of the present invention include renal, urothelial, colon, rectal, lung, and breast cancerous tissue and cancerous tissue of metastatic adenocarcinoma to the liver.

Use of the methods of the present invention has a number of benefits. Since the biological agents according to the present invention only bind to cancerous cells and prostate epithelial cells, the method is selective for these types of cells. As a result, the sensitivity and selectivity of the method are high. In addition, the ability to distinguish between living and dead prostate cells may be advantageous, especially to monitor the effectiveness of a particular treatment.

Hybridomas E99, J415, J533, and J591 have been deposited pursuant to, and in satisfaction of, the requirements of the Budapest Treaty on the International Recognition of the Deposit of Microorganisms for the Purposes of Patent Procedure with the American Type Culture Collection ("ATCC") at 12301 Parklawn Drive, Rockville, Md. 20852. Hybridoma E99 was deposited on May 2, 1996 and received ATCC Designation Number HB-12101. Hybridoma J415 was deposited on May 30, 1996, and received ATCC Designation Number HB-12109. Hybridomas J533 and J591 were deposited on Jun. 6, 1996, and received ATCC Designation Numbers HB-12127 and HB-12126, respectively.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various publications and patents are cited in parenthesis. Their contents are hereby incorporated by reference into the present application.

What is claimed is:

1. A method for isolating viable epithelial cells from a solution, the method comprising:

providing an atibody or antigen-binding portion thereof which binds to an extracellular domain of prostate specific membrane antigen (PSMA);

contacting said antibody or antigen-binding portion thereof with a magnetizable medium under conditions permitting binding of said antibody or antigen-binding portion thereof to said magnetizable medium;

contacting a solution containing said epithelial cells with said magnetizable medium bound to said antibody or antigen-binding portion thereof under conditions permitting binding of said antibody or antigen-binding portion thereof to said epithelial cells to form a complex including said magnetizable medium, said antibody or antigen-binding portion thereof, and said epithelial cells;

contacting said complex with a magnetized matrix under conditions permitting isolation of said complex from said solution; and eluting said epithelial cells from said magnetized matrix.

2. The method of claim 1, wherein said antibody or antigen-binding portion thereof is selected from the group consisting of a monoclonal antibody, a polyclonal antibody, an F(ab), an F(ab')$_2$, and an F$_v$.

3. The method of claim 1, wherein said antibody is a monoclonal antibody produced by a hybridoma cell line having an ATCC Accession Number selected from the group consisting of HB-12101, HB12109, HB-12127, and HB-12126.

4. The method of claim 1, wherein said solution comprises a tissue culture medium.

5. The method of claim 1, wherein said antibody or antigen-binding portion thereof is a monoclonal antibody.

6. The method of claim 5, wherein said monoclonal antibody is selected from the group consisting of an E99, a J415, a J533, and a J591 monoclonal antibody.

7. The method of claim 5, wherein said monoclonal antibody is a J591 monoclonal antibody.

8. The method of claim 1, wherein said epithelial cells are selected from the group consisting of normal epithelial cells, benign hyperplastic epithelial cells, cancerous epithelial cells, normal prostate epithelial cells, benign hyperplastic prostate epithelial cells, and cancerous prostate epithelial cells.

9. The method of claim 8, wherein said epithelial cells are cancerous prostate epithelial cells.

10. The method of claim 9, wherein said cancerous prostate epithelial cells are prostatic adenocarcinoma cells.

11. The method of claim 1, wherein said magnetized matrix is a magnetic activated cell sorter (MACS).

12. The method of claim 1, wherein said magnetized matrix is in the form of a separating column.

13. The method of claim 1, wherein said solution comprises a biological fluid.

14. The method of claim 13, wherein said biological fluid is selected from the group consisting of blood, urine, semen, seminal fluid, lymph, cerebrospinal fluid, mucus, tears, sweat, gastric fluid, saliva, synovial fluid, and a bone marrow suspension.

15. The method of claim 13, wherein said biological fluid comprises semen.

16. A method for isolating cancerous vascular endothelial cells from a solution, the method comprising:

providing an antibody or antigen-binding portion thereof which binds to an extracellular domain of prostate specific membrane antigen (PSMA);

contacting said antibody or antigen-binding portion thereof with a magnetizable medium under conditions permitting binding of said antibody or antigen-binding portion thereof to said magnetizable medium;

contacting a solution containing said cancerous vascular endothelial cells with said magnetizable medium bound to said antibody or antigen-binding portion thereof under conditions permitting binding of said antibody or antigen-binding portion thereof to said cancerous vascular endothelial cells to form a complex containing said magnetizable medium, said antibody or antigen-binding portion thereof, and said cancerous vascular endothelial cells;

contacting said complex with a magnetized matrix under conditions permitting isolation of said of said complex from said solution; and eluting said epithelial cells from said magnetized matrix.

* * * * *

UNITED STATES PATENT AND TRADEMARK OFFICE
CERTIFICATE OF CORRECTION

PATENT NO.    : 6,653,129 B1
DATED         : November 25, 2003
INVENTOR(S)   : Neil Bander, Leonard Michael Glode and Chang In Suh It is certified that error appears in the above-identified patent and that said Letters Patent is hereby corrected as shown below:

Title page,
Item [73], Assignee, after "The Regents of the University of Colorado, Denver, CO (US)", insert -- and Cornell Research Foundation, Inc., Ithaca, NY (US) --.

Signed and Sealed this

Twenty-eighth Day of February, 2006

JON W. DUDAS
*Director of the United States Patent and Trademark Office*